United States Patent
Goldenberg et al.

(10) Patent No.: US 6,245,740 B1
(45) Date of Patent: *Jun. 12, 2001

(54) POLYOL:OIL SUSPENSIONS FOR THE SUSTAINED RELEASE OF PROTEINS

(75) Inventors: Merrill Goldenberg; Daxian Shan; Alice Beekman, all of Thousand Oaks, CA (US)

(73) Assignee: Amgen Inc., Thousand Oaks, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/221,181

(22) Filed: Dec. 23, 1998

(51) Int. Cl.$^7$ .................................................. A61K 38/18
(52) U.S. Cl. .......................... 514/12; 514/964; 514/965; 530/399; 435/69.1
(58) Field of Search ........................... 514/12, 964, 965; 435/69.1; 530/399; 424/85.4

(56) References Cited

U.S. PATENT DOCUMENTS

| | | | |
|---|---|---|---|
| 2,491,537 | 12/1949 | Welch | 167/58 |
| 2,507,193 | 5/1950 | Buckwalter | 167/65 |
| 2,964,448 | 12/1960 | Anschel | 167/74 |
| 4,371,523 | 2/1983 | Grodsky | 424/178 |
| 4,439,181 * | 3/1984 | Blackshear et al. | 604/56 |
| 4,675,189 | 6/1987 | Blackshear | 128/213 |
| 4,695,463 | 9/1987 | Kent | 424/490 |
| 4,695,623 | 9/1987 | Yang | 424/440 |
| 4,703,008 | 10/1987 | Kin | 435/240.2 |
| 4,810,643 | 3/1989 | Souza | 435/91 |
| 4,855,134 | 8/1989 | Yamahira | 424/85.7 |
| 4,897,471 | 1/1990 | Stabinsky | 536/27 |
| 4,977,140 | 12/1990 | Ferguson | 514/12 |
| 4,999,291 | 3/1991 | Souza | 435/69.1 |
| 5,075,222 | 12/1991 | Hannum | 435/69.1 |
| 5,372,808 | 12/1994 | Blatt | 424/85.5 |
| 5,411,951 * | 5/1995 | Mitchell | 514/12 |
| 5,441,868 | 8/1995 | Lin | 435/69.4 |
| 5,541,293 | 7/1996 | Stabinsky | 530/351 |
| 5,547,933 | 8/1996 | Lin | 514/8 |
| 5,581,476 | 12/1996 | Osslund | 364/496 |
| 5,582,823 | 12/1996 | Souza | 514/2 |
| 5,618,698 | 4/1997 | Lin | 435/69.4 |
| 5,621,080 | 4/1997 | Lin | 435/320.1 |
| 5,789,198 * | 8/1998 | Akerblom | 435/69.1 |

FOREIGN PATENT DOCUMENTS

| | | |
|---|---|---|
| 76380/91 | 11/1991 | (AU) . |
| 10948/92 | 8/1992 | (AU) . |
| 0 243 153 | 10/1987 | (EP) . |
| 0 335 423 | 10/1989 | (EP) . |
| 0 374 120 | 6/1990 | (EP) . |
| 0 459 630 | 12/1991 | (EP) . |
| 0 473 268 | 3/1992 | (EP) . |
| 0 272 703 | 10/1997 | (EP) . |
| WO 85/02118 | 5/1985 | (WO) . |
| WO 89/10932 | 11/1989 | (WO) . |
| WO 91/05795 | 5/1991 | (WO) . |
| WO 91/05798 | 5/1991 | (WO) . |
| WO 92/17505 | 10/1992 | (WO) . |
| WO 94/00913 | 1/1994 | (WO) . |
| WO 94/09257 | 4/1994 | (WO) . |
| WO 94/17185 | 8/1994 | (WO) . |
| WO 95/17206 | 6/1995 | (WO) . |
| WO 96/05309 | 2/1996 | (WO) . |
| WO 96/18417 | 6/1996 | (WO) . |
| WO 96/40912 | 12/1996 | (WO) . |
| WO 97/00128 | 1/1997 | (WO) . |
| WO 97/01010 | 1/1997 | (WO) . |
| WO 97/01331 | 1/1997 | (WO) . |
| WO 97/06816 | 2/1997 | (WO) . |
| WO 97/23614 | 7/1997 | (WO) . |

OTHER PUBLICATIONS

HSieng S. Lu, et al., "Folding and Oxidation of Recombinant Human Granulocyte Colony Stimulating Factor Produced in *Escherichia coli*", *The Journal of Biological Chemistry*, vol. 267(13), pp. 8770–8777 (1992).

Hutchinson, F.G., et al., "Biodegradable Polymers for the Sustained Release of Peptides", *Biochemical Society Transactions*, vol. 13, pp. 520–523, (1985).

Jackanicz, T.M., "Polylactic Acid as a Biodegradable Carrier for Contraceptive Steroids", *Contraception*, vol. 8(3) pp. 227–234, (1973).

Ford, C.F., et al., "Fusion Tails for the Recovery and Purification of Recombinant Proteins", *Protein Expression and Purification*, vol. 2, pp. 95–107, (1991).

* cited by examiner

Primary Examiner—F. T. Moezie
(74) *Attorney, Agent, or Firm*—Craig A. Crandall; Ron K. Levy; Steven M. Odre

(57) ABSTRACT

The present invention relates to the preparation of polyol/thickened oil suspensions containing a biologically active agent, for the sustained delivery of the biologically active agent. The described protein/glycerol/oil suspensions show sustained release of protein, e.g., G-CSF, of up to at least one week.

8 Claims, No Drawings

POLYOL:OIL SUSPENSIONS FOR THE SUSTAINED RELEASE OF PROTEINS

FIELD OF THE INVENTION

The present invention relates to the preparation of polyol/thickened oil suspensions containing a biologically active agent, for the sustained delivery of the biologically active agent.

BACKGROUND OF THE INVENTION

Due to recent advances in genetic and cell engineering technologies, proteins known to exhibit various pharmacological actions in vivo are capable of being produced in large amounts for pharmaceutical applications. Such pharmaceutical proteins include erythropoietin (EPO), novel erythropoiesis stimulating protein (NESP), granulocyte colony-stimulating factor (G-CSF), interferons (alpha, beta, gamma, consensus), tumor necrosis factor binding protein (TNFbp), interleukin-1 receptor antagonist (IL-1ra), brain-derived neurotrophic factor (BDNF), kerantinocyte growth factor (KGF), stem cell factor (SCF), megakaryocyte growth differentiation factor (MGDF), osteoprotegerin (OPG), glial cell line derived neurotrophic factor (GDNF), somatotrophins and obesity protein (OB protein). OB protein may also be referred to herein as leptin.

Many illnesses or conditions treated with pharmaceutical proteins require sustained protein levels to achieve the most effective therapeutic result. However, as with most protein pharmaceuticals, the generally short biological half-life requires frequent administration. These repeated injections are given at various intervals which result in fluctuating medication levels at a significant physical and monetary burden on the patients. Since many conditions respond better to controlled levels of a pharmaceutical, a need exists for controlled release of a medicament to provide longer periods of consistent release. Such sustained-release medicaments would provide a means of controlling blood levels of the active ingredient, thus providing the patient with enhanced prophylactic, therapeutic or diagnostic effects, as well as greater safety, patient convenience and patient compliance. Also such sustained release compositions can lead to dose sparing and thus lower cost of protein production. Unfortunately, the instability of most proteins (e.g. denaturation and loss of bioactivity upon exposure to heat, organic solvents, etc.) has greatly limited the development and evaluation of sustained-release formulations.

Attempts to develop sustained-release formulations have included the use of a variety of biodegradable and non-biodegradable polymer (e.g. poly(lactide-co-glycolide)) microparticles containing the active ingredient (see e.g., Wise et al., *Contraception,* 8:227–234 (1973); and Hutchinson et al., *Biochem. Soc. Trans.,* 13:520–523 (1985)), and a variety of techniques are known by which active agents, e.g. proteins, can be incorporated into polymeric microspheres (see e.g., U.S. Pat. No. 4,675,189 and references cited therein). Unfortunately, some of the sustained release devices utilizing microparticles still suffer from such things as: low entrapment efficiency; active agent aggregation formation; high initial bursts of active agent with minimal release thereafter; and incomplete release of active agent.

Other drug-loaded polymeric devices have also been investigated for long term, therapeutic treatment of various diseases, again with much attention being directed to polymers derived from alpha hydroxycarboxylic acids, especially lactic acid in both its racemic and optically active form, and glycolic acid, and copolymers thereof. These polymers are commercially available and have been utilized in FDA-approved systems, e.g., the Lupron Depot™, which consists of injectable microparticles which release leuprolide acetate for about 30 days for the treatment of prostate cancer.

Various problems identified with the use of such polymers include: inability of certain macromolecules to diffuse out through the matrix; deterioration and decomposition of the drug (e.g., denaturation caused by the use of organic solvents); irritation to the organism (e.g. side effects due to use of organic solvents); low biodegradability (such as that which occurs with polycondensation of a polymer with a multifunctional alcohol or multifunctional carboxylic acid, i.e., ointments); and slow rates of degradation.

A variety of oil based formulations have been described. Welch in U.S. Pat. No. 2,491,537 discloses the use of oil suspensions (gelled vegetable oil) to provide 24 hour release of penicillin. Buckwalter in U.S. Pat. No. 2,507,193 discloses release in rabbits for up to eleven days using procaine penicillin suspended in peanut oil gelled with 5% aluminum monostearate (AIMS). Anschel in U.S. Pat. No. 2,964,448 discloses suspensions of relaxin in a vegetable oil gelled with AIMS. Anschel reports 5–7 days of relaxation and discloses longer effect (up to 23 days) by heat treating the suspension containing AIMS. Yamahira et al. in U.S. Pat. No. 4,855,134 disclose sustained-release preparations of indomethacin or interferon in admixture with a pharmaceutically acceptable biodegradable carrier, e.g., gelatin. Mitchell in U.S. Pat. No. 5,411,951 discloses compositions wherein metal-associated somatotropin is present in a biocompatible oil and it is demonstrated that the compositions can be parenterally administered for prolonged release of somatotropin in animals. Ferguson et al. in U.S. Pat. No. 4,977,140 disclose sustained release formulations comprising bovine somatotropin, a wax, and an oil. Reichert et al. in WO 96/18417 disclose pharmaceutical compositions comprising mixtures of crystalline G-CSF and vegetable oils.

There have also been a number of reports discussing efforts to develop drug delivery systems utilizing protein that are subject to aggregation. For example, Grodsky et al., U.S. Pat. No. 4,371,523, describe the use of anti-aggregation agents, e.g., glutamic acid and/or aspartic acid, to develop insulin formulations. Blackshear et al., U.S. Pat. No. 4,439,181, describe mixing glycerol or another polyol with an aqueous protein hormone solution prior to the introduction of the solution into the drug delivery system. Wigness et al., PCT Publication WO 85/02118 describe the use of glycerol to prevent precipitation of proteins within drug delivery systems; and Azain et al., EP Publication 0 374 120 A2 describe stable somatotropin compositions which utilize, inter alia, a stabilizing polyol.

Despite the advances made in the processes described above, there is still a need to develop pharmaceutical formulations which achieve a more versatile and effective means of sustained-release for clinical applications. Numerous recombinant or natural proteins could benefit from constant long term release and thereby provide more effective clinical results.

Human recombinant G-CSF selectively stimulates neutrophils, a type of white blood cell used for fighting infection. Currently, Filgrastim®, a recombinant G-CSF, is available for therapeutic use. The structure of G-CSF under various conditions has been extensively studied; Lu et al., *J. Biol. Chem.* Vol. 267, 8770–8777 (1992).

G-CSF is labile and highly susceptible to environmental factors such as temperature, humidity, oxygen and ultraviolet rays. And, because of its hydrophobic characteristics, G-CSF is difficult to formulate due to formation of dimer and higher order aggregates (macro range) during long-term storage. G-CSF has been shown to be very prone to aggregation, especially at neutral pH, elevated salt and temperatures (i.e. physiological serum conditions). This instability makes the sustained release (of a period of one week or greater) by conventional delivery systems very problematic, and in fact, such systems generally provide only a few days of release at best.

It is an object of the present invention to produce a G-CSF-containing preparation which would provide for the sustained release of G-CSF. Production of such preparations is achieved using glycerol/oil suspensions containing G-CSF, and, importantly, pharmaceutical compositions using these G-CSF/glycerol/oil suspensions are capable of providing increased bioavailability, protein protection, decreased degradation and slow release with increased protein stability and potency. Importantly, pharmaceutical compositions of the present invention provide a simple, rapid and inexpensive means of controlled recombinant protein release for effective prophylactic, therapeutic or diagnostic results.

SUMMARY OF THE INVENTION

The present invention thus relates to the preparation of a stabilized, prolonged-release injectable suspension containing a biologically active agent. The present invention stems from the observation that G-CSF powder is stabilized when suspended in glycerol and remains stabilized when the suspension is further suspended in a thickened oil such as sesame oil containing a low percentage of aluminum monostearate, or wax, thus providing a stabilized, prolonged-release injectable preparation. Importantly, the methods described herein are broadly applicable to other proteins (or analogs thereof), as well as G-CSF.

In one embodiment, the present invention provides pharmaceutical compositions comprising an effective amount of a biologically active agent (BAA) incorporated into a polyol/thickened oil suspension, said biologically active agent in the form of a powder or aqueous solution, and said suspension capable of providing for the sustained-release of the biologically active agent.

In another embodiment, the present invention provides a method for the parenteral administration of a BAA/glycerol/oil suspension to a warm blooded animal, wherein said suspension is administered subcutaneously, or intramuscularly and the biologically active agent is released from the suspension at a controlled rate for up to one week or more.

The present invention further relates to processes for preparing sustained-release injectable pharmaceutical compositions of BAA/polyol/oil suspensions as above. The principal embodiment comprises: (a) suspending a BAA in a polyol to form a BAA/polyol suspension; and (b) suspending said BAA/polyol suspension in a mixture comprising a thickened oil, or wax, to form a BAA/polyol/oil suspension.

The present invention further relates to a prefilled syringe comprising said formulation.

The present invention also relates to methods of treatment of individuals using the stabilized, prolonged-release injectable preparations described herein.

DETAILED DESCRIPTION OF THE INVENTION

As used herein, the following terms shall have the following meaning:

"Biodegradable" is defined as meaning that the polyol/oil vehicle will erode or degrade or absorb or metabolize in vivo to form smaller non-toxic components.

"Biocompatible" is defined as meaning the oil and its thickeners and other excipients will have no intolerable adverse effect on the polypeptide, or human being treated.

"Parenteral administration" is defined as meaning any route of administration other than the alimentary canal, including, for example, subcutaneous, intramuscular, intrathecal, intraorbital, intraarticular, pulmonary, nasal, rectal and otic.

As used herein, biologically active agents refers to recombinant or naturally occurring proteins, whether human or animal, useful for prophylactic, therapeutic or diagnostic application. The biologically active agent can be natural, synthetic, semi-synthetic or derivatives thereof. In addition, biologically active agents of the present invention can be PEGylated or conjugated with water soluble adducts such as carbohydrates, e.g., dextran. A wide range of biologically active agents are contemplated. These include but are not limited to hormones, cytokines, hematopoietic factors, growth factors, antiobesity factors, trophic factors, anti-inflammatory factors, and enzymes (see also U.S. Pat. No. 4,695,463 for additional examples of useful biologically active agents). One skilled in the art will readily be able to adapt a desired biologically active agent to the compositions of present invention which can also include small organic or organometallic compounds.

Such proteins would include but are not limited to granulocyte-colony stimulating factors (G-CSF's) (see, U.S. Pat. Nos. 4,810,643, 4,999,291, 5,581,476, 5,582,823, and PCT Publication No. 94/17185, hereby incorporated by reference including drawings), interferons (see, U.S. Pat. Nos. 5,372,808, 5,541,293 4,897,471, and 4,695,623 hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), stem cell factor (PCT Publication Nos. 91/05795, 92/17505 and 95/17206, hereby incorporated by reference including drawings), osteoprotegerin (PCT Publication No. 97/23614, hereby incorporated by reference including drawings), novel erythropoiesis stimulating protein (NESP) (PCT Publication No. 94/09257, hereby incorporated by reference including drawings) and leptin (OB protein).

Provided below is a working example using G-CSF, which, as described above, is a therapeutic protein used to treat hematopoietic disorders. In general, G-CSF useful in the practice of this invention may be a form isolated from mammalian organisms or, alternatively, a product of chemical synthetic procedures or of prokaryotic or eukaryotic host expression of exogenous DNA sequences obtained by genomic or cDNA cloning or by DNA synthesis. Suitable prokaryotic hosts include various bacteria (e.g., E. coli); suitable eukaryotic hosts include yeast (e.g., S. cerevisiae) and mammalian cells (e.g., Chinese hamster ovary cells, monkey cells). Depending upon the host employed, the G-CSF expression product may be glycosylated with mammalian or other eukaryotic carbohydrates, or it may be non-glycosylated. The G-CSF expression product may also include an initial methionine amino acid residue (at position −1). The present invention contemplates the use of any and all such forms of G-CSF, although recombinant G-CSF, especially E. coli derived, is preferred, for, among other things, greatest commercial practicality.

Certain G-CSF analogs have been reported to be biologically functional, and these may also be chemically modified, by, for example, the addition of one or more polyethylene glycol molecules. G-CSF analogs are reported in U.S. Pat. No. 4,810,643. Examples of other G-CSF analogs which have been reported to have biological activity are those set forth in AU-A-76380/91, EP O 459 630, EP O 272 703, EP O 473 268 and EP O 335 423, although no representation is made with regard to the activity of each analog reportedly disclosed. See also AU-A-10948/92, PCT 94/00913 and EP 0 243 153. Of course, if one so desires when treating non-human mammals, one may use recombinant non-human G-CSF's, such as recombinant murine, bovine, canine, etc. See PCT WO 9105798 and PCT WO 8910932, for example.

The type of G-CSF used for the present preparations may be selected from those described in PCT Publication No. 94/17185, as cited above and herein incorporated by reference in its entirety. The 174 amino acid sequence for mature, recombinant methionyl human G-CSF is presented herein as SEQ ID NO: 1, where the first amino acid of the mature protein is threonine (T) (at position 1) and a methionyl residue is located at position −1 (not included in the sequence below).

| | | | | | SEQ ID NO: 1 | | | | | | | |
|---|---|---|---|---|---|---|---|---|---|---|---|---|
| | T | P | L | G | P | A | S | S | L | P | Q | S | F | L |
| L | K | C | L | E | Q | V | R | K | I | Q | G | D | G | A |
| A | L | Q | E | K | L | C | A | T | Y | K | L | C | H | P |
| E | E | L | V | L | L | G | H | S | L | G | I | P | W | A |
| P | L | S | S | C | P | S | Q | A | L | Q | L | A | G | C |
| L | S | Q | L | H | S | G | L | F | L | Y | Q | G | L | L |
| Q | A | L | E | G | I | S | P | E | L | G | P | T | L | D |
| T | L | Q | L | D | V | A | D | F | A | T | T | I | W | Q |
| Q | M | E | E | L | G | M | A | P | A | L | Q | P | T | Q |
| G | A | M | P | A | F | A | S | A | F | Q | R | R | A | G |
| G | V | L | V | A | S | H | L | Q | S | F | L | E | V | S |
| Y | R | V | L | R | H | L | A | Q | P | | | | | |

However, as with any of the present G-CSF moieties, the methionyl residue at position −1 may be absent.

Also included are those proteins as set forth above with amino acid substitutions which are "conservative" according to acidity, charge, hydrophobicity, polarity, size or any other characteristic known to those skilled in the art. These are set forth in Table 1, below. See generally, Creighton, *Proteins, passim* (W.H. Freeman and Company, N.Y., 1984); Ford et al., *Protein Expression and Purification* 2:95–107 (1991), which are herein incorporated by reference.

TABLE 1

| Conservative Amino Acid Substitutions | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |

TABLE 1-continued

| Conservative Amino Acid Substitutions | |
|---|---|
| Aromatic: | phenylalanine |
| | tryptophan |
| | tyrosine |
| Small: | glycine |
| | alanine |
| | serine |
| | threonine |
| | methionine |

In addition, biologically active agents can also include but are not limited to, insulin, gastrin, prolactin, adrenocorticotropic hormone (ACTH), thyroid stimulating hormone (TSH), luteinizing hormone (LH), follicle stimulating hormone (FSH), human chorionic gonadotropin (HCG), motilin, interferons (alpha, beta, gamma), interleukins (IL-1 to IL-12), tumor necrosis factor (TNF), tumor necrosis factor-binding protein (TNF-bp), brain derived neurotrophic factor (BDNF), glial derived neurotrophic factor (GDNF), neurotrophic factor 3 (NT3), fibroblast growth factors (FGF), neurotrophic growth factor (NGF), insulin-like growth factors (IGFs), macrophage colony stimulating factor (M-CSF), granulocyte macrophage colony stimulating factor (GM-CSF), megakaryocyte derived growth factor (MGDF), keratinocyte growth factor (KGF), thrombopoietin, platelet-derived growth factor (PGDF), colony simulating growth factors (CSFs), bone morphogenic protein (BMP), superoxide dismutase (SOD), tissue plasminogen activator (TPA), urokinase, somatotropins, streptokinase and kallikrein. The term proteins, as used herein, includes peptides, polypeptides, consensus molecules, analogs, derivatives or combinations thereof.

The BAA used to prepare the sustained-release compositions of the present invention can be in solution or powder form and is first admixed with a polyol, e.g., glycerol. The BAA can be in the form of a powder in glycerol or dissolved or suspended in an aqueous solution of glycerol. The polyol is added in an amount sufficient to stabilize (e.g., prevent aggregation) of the BAA during long-term storage of the BAA in the suspension.

Other biocompatible C-4 to C-19 polyols contemplated for use include, but are not limited to, C-4: erythritol; C-5: arabinose, xylose, ribose; C-6: inositol, fructose, galactose, glucose, mannose; C-12: maltose and sucrose. If the polyol used is in solid form, it will be first prepared as an aqueous or aqueous organic solution or fluidized by means of heat or pressure, and admixed with the BAA. The level of polyol used can preferably range from 5%–90%, more preferably from 10%–50%, and most preferably from 10%–30% by weight. In a preferred embodiment wherein G-CSF is the biologically active agent and glycerol is the polyol, 20% aqueous glycerol is used. In other preferred embodiments, where little or no water is present, 20% glycerol is with respect to the total volume of the formulation.

The oils used in the present invention are biocompatible, of low acidity and essentially free from rancidity. Such oils are selected from the group consisting of, for example, sesame seed, cannola, saffron, castor, cottonseed, olive, peanut, sunflower seed, ethyl oleate, vitamin E including α-tocopherol and its derivatives, and Miglyol 812.

The glycerol/oil suspensions will also contain a "thickener" or "gelling agent" which serves to retard hydration of the suspension, give the body of oil greater viscosity or viscoelasticity, and thereby decrease the rate of release of the BAA from the suspension following administration and also increase the stabilization of the BAA, and increase the physical stability of the suspension as a whole (i.e., prevent phase separation). Such agents include polyvalent metal salts of organic acids, e.g., aluminum, zinc, magnesium or calcium salts of lauric acid, palmitic acid, stearic acid and the like, and oleaginous materials such as waxes and high viscosity oils and organic or inorganic fillers such as polymers and salts. Aluminum monostearate and distearate and white wax are particularly preferred agents. Said agents are usually present at concentrations (based on weight of oil) of between about 0.1% and about 99%, more typically between about 0.5% and about 90% and for metal salts even more typically 0.5% to 20%. This ratio is important for purposes of assuring that the agent doesn't increase the viscosity of the suspension to the point where the suspension is no longer useful for injection through a syringe. For highly viscous formulations, implants are also contemplated.

The glycerol/oil suspensions may further comprise surface active agents or emulsifiers to stabilize the glycerol/oil suspension and prevent it from separating. This surface active agent or emulsifier can be ionic or nonionic and may be selected from the group consisting of, for example, Span 40, Span 80, Pluronics®, and egg lecithin, or mixtures thereof, preferably with a HLB (hydrophile-lipophile balance) of 1–10, more preferably 2–8, and even more preferably 4–8. The surfactant can also help dissipate the oil in the biological environment. The surfactant is usually present at 0.1% to 50%, preferably 0.2% to 20%, and more preferably 0.5% to 10% by weight of oil. Certain materials, such as hydrogenated vegetable oil can function as both a thickener and stabilizer of the glycerol suspension.

The BAA/glycerol/oil suspensions of the present invention can be prepared by suspending a biologically active agent (in powdered form) in substantially pure glycerol solution to form a BAA/glycerol suspension, and then suspending said BAA/glycerol suspension in a solution comprising oil alone or oil containing a "gelling agent" suspended or dissolved in the oil. The oil (containing gelling agent) may first need to be heated (with mixing) to assure that the gelling agent completely dissolves in the oil. The BAA formulation can also be prepared by dissolving or suspending the BAA in aqueous glycerol solution (preferably containing a surfactant) and mixing the solution into an oil (preferably containing a surfactant), and where aqueous glycerol is preferably buffered at a stable pH (e.g., acidic for G-CSF). The aqueous phase preferably contains a moderate to high HLB and the oil phase preferably contains a low HLB surfactant. In the present invention, moderate to high HLB is greater than about 8, and low HLB is lower than about 8.

In general, comprehended by the invention are pharmaceutical compositions comprising effective amounts of biologically active agent, or derivative products (e.g., precipitates), together with pharmaceutically acceptable diluents, preservatives, solubilizers, emulsifiers, antioxidants (e.g., ascorbic acid and Vitamin E), adjuvants and/or carriers needed for administration. (See PCT 97/01331 hereby incorporated by reference.) The optimal pharmaceutical formulation for a desired biologically active agent will be determined by one skilled in the art depending upon the route of administration, desired dosage and duration of release. Exemplary pharmaceutical compositions are disclosed in Remington's Pharmaceutical Sciences (Mack Publishing Co., 18th Ed., Easton, Pa., pgs. 1435–1712 (1990)). The pharmaceutical compositions of the present invention are particularly attractive for parenteral administration, e.g., by injection intramuscularly, subcutaneously, or intraperitoneally.

Therapeutic uses of the compositions of the present invention depend on the biologically active agent used. One skilled in the art will readily be able to adapt a desired biologically active agent to the present invention for its intended therapeutic uses. Therapeutic uses for such agents are set forth in greater detail in the following publications hereby incorporated by reference including drawings. Therapeutic uses include but are not limited to uses for proteins like granulocyte-colony stimulating factors (see, U.S. Pat. Nos. 4,999,291, 5,581,476, 5,582,823, 4,810,643 and PCT Publication No. 94/17185, hereby incorporated by reference including drawings), interferons (see, U.S. Pat. Nos. 5,372,808, 5,541,293, hereby incorporated by reference including drawings), interleukins (see, U.S. Pat. No. 5,075,222, hereby incorporated by reference including drawings), erythropoietins (see, U.S. Pat. Nos. 4,703,008, 5,441,868, 5,618,698 5,547,933, and 5,621,080 hereby incorporated by reference including drawings), stem cell factor (PCT Publication Nos. 91/05795, 92/17505 and 95/17206, hereby incorporated by reference including drawings), OB protein (see PCT publication Nos. 96/40912, 96/05309, 97/00128, 97/01010 and 97/06816 hereby incorporated by reference including figures), novel erythropoiesis stimulating protein (PCT Publication No. 94/09257, hereby incorporated by reference including drawings), and small molecule drugs. In addition, the present compositions may also be used for manufacture of one or more medicaments for treatment or amelioration of the conditions the biologically active agent is intended to treat.

One skilled in the art will be able to ascertain effective dosages by administration and observing the desired therapeutic effect. Preferably, for G-CSF, the formulation of the suspension will be such that between about 0.01 μg G-CSF moiety/kg body weight/day and 10 mg G-CSF moiety/kg body weight/day will yield the desired therapeutic effect. The effective dosages may be determined using diagnostic tools over time. For example, a diagnostic for measuring the amount of G-CSF in the blood (or plasma or serum) may first be used to determine endogenous levels of G-CSF protein. Such diagnostic tool may be in the form of an antibody assay, such as an antibody sandwich assay. The amount of endogenous G-CSF protein is quantified initially, and a baseline is determined. The therapeutic dosages are determined as the quantification of endogenous and exogenous G-CSF protein moiety (that is, protein, analog or derivative found within the body, either self-produced or administered) is continued over the course of therapy. The dosages may therefore vary over the course of therapy, with, for example, a relatively high dosage being used initially, until therapeutic benefit is seen, and lower dosages used to maintain the therapeutic benefits. Alternatively, the levels of neutrophils are determined and monitored over the course of the therapy. The dosage is adjusted to maintain the required level of neutrophil counts with the lowest frequency of injections.

The following examples are offered to more fully illustrate the invention, but are not to be construed as limiting the scope thereof.

EXAMPLE 1

This example describes the preparation of G-CSF powder by spray-drying.

G-CSF solution (~2.75 mg/ml, with 5% sorbitol, in 0.58 mM HCl ) was placed in dialysis tubing (Spectrum Lab Inc., flat width 18±2 mm, diameter 11.5 mm, 1.0 ml/cm), and dialyzed against water (pH 3.25) at 4° C. for 24 hours. During the dialysis, the water is changed four times. Dialyzed G-CSF solution (~1100 ml) was then placed in an ultrafiltration cell and air pressure applied on the solution. After two hours, about 300 ml of concentrated G-CSF solution was collected and filtered through a 0.2 mm filter unit. The concentration of the final G-CSF solution is 9.134 mg/ml. The spray-drying was performed on a BUCHI 190 Mini Spray Dryer (Brinkmann Institute), and all of the glassware of the spray dryer was first washed with deionized water, followed by sterile water, followed by ethanol. The spray-drying was performed with inlet air flow of 450 normal liters/hour, and the feed rate of G-CSF CSF solution was 1.0 ml/min. G-CSF powder (2.640 grams, 82.7% G-CSF) was obtained from the 290 mL starting G-CSF solution.

EXAMPLE 2

This example describes the preparation of G-CSF/ glycerol suspensions and the use of the G-CSF/glycerol suspensions to prepare G-CSF/glycerol/oil formulations.

Step 1. A G-CSF/glycerol suspension was first prepared by placing 105.4 milligrams G-CSF spray-dried powder (prepared as described in Example 1) and 2.401 mL glycerol in a mortar and grinding the mixture until no course particles were seen.

Step 2. A thickened oil suspension was then prepared by placing 45.67 grams sesame oil (Croda, Inc.) and 1.91 grams aluminum monostearate (AIMS)(Fluka) in a 125 mL erlenmeyer flask and mixing with a magnetic stirrer at room temperature for 20 minutes, followed by heating at 165° C.–170° C. under nitrogen atmosphere with stirring. The stirring is continued for two hours, and the mixture then cooled to room temperature, resulting in an opalescent gel-like thickened oil (3% AIMS).

Step 3. One mL G-CSF/glycerol suspension and 4 mL thickened oil were placed in a mortar and ground together until well mixed. The suspension (G-CSF/20% glycerol/3% AIMS/oil) was stored in a sterile sample vial at 4° C. until needed.

EXAMPLE 3

This example describes the preparation of a G-CSF/glycerol-containing viscous oil suspension further containing L-ascorbic acid and surfactant.

L-Ascorbic acid (50 mg) was dissolved in a 1 mL glycerol solution by heating and stirring the mixture. After being cooled to room temperature, the ascorbic acid/glycerol solution was mixed with GCSF powder (45.3 mg) and Span 80 (250 mL). 3.75 mL thickened oil (3% AIMS) prepared as described above was added to the G-CSF/ascorbic acid/glycerol mixture and ground together to give a viscous oil suspension (G-CSF/20% glycerol+ascorbic acid/Span 80/3% AIMS/oil).

EXAMPLE 4

This example shows the preparation of an oil thickened with 7% white wax.

The thickened 7% wax/oil was produced (using the procedure described in Example 2, Step 2) by heating a mixture of white wax (4.49 grams) and sesame oil (59.65 grams) at 160° C. under nitrogen atmosphere for 2 hours.

EXAMPLE 5

This example shows the preparation of various G-CSF-containing oil formulations using 7% wax as thickener and with different glycerol levels.

Preparation 1: G-CSF powder (27.6 mg) and glycerol (600 μL) were mixed in a mortar and ground until no observable coarse particles were seen. Then 2.4 mL of the thickened 7% wax/oil prepared as described in Example 4 was added to the GCSF/glycerol suspension. The mixture was ground together with mortar and pestle to give a viscous oil formulation (G-CSF/20% glycerol/7% wax).

Preparation 2: GCSF powder (45.3 mg) was mixed with 1.00 ml of ascorbic acid/glycerol solution (prepared as described in Example 3), an then 4.0 mL of thickened 7% wax/oil was added. The resulting mixture was ground together to give a viscous oil formulation (G-CSF/20% glycerol+ascorbic acid/7% wax.

Preparation 3: G-CSF powder (27.3 mg) and glycerol (450 μL) were mixed in a mortar and ground until no observable coarse particles were seen. Then 2.55 mL of the thickened 7% wax/oil prepared as described in Example 4 was added to the GCSF/glycerol suspension. The mixture was ground together with mortar and pestle to give a viscous oil formulation (G-CSF/15% glycerol/7% wax).

Preparation 4: G-CSF powder (27.5 mg) and glycerol (750 μL) were mixed in a mortar and ground until no observable coarse particles were seen. Then 2.25 mL of the thickened 7% wax/oil prepared as described in Example 4 was added to the GCSF/glycerol suspension. The mixture was ground together with mortar and pestle to give a viscous oil formulation (G-CSF/25% glycerol/7% wax).

EXAMPLE 6

This example shows the preparation of an G-CSF/glycerol oil thickened with 10% white wax.

The thickened 10% wax/oil was produced (using the procedure described in Example 2, Step 2) by heating a mixture of white wax (6.5 grams) and sesame oil (58.5 grams) at 160° C. under nitrogen atmosphere for 2 hours.

GCSF powder (27.4 mg) and glycerol (600 μl) were mixed together, and then 2.40 mL of thickened oil (10% wax) was added to the GCSF/glycerol suspension. The mixture was ground to give a viscous oil formulation (G-CSF/20% glycerol/10% wax).

EXAMPLE 7

This example describes the in vivo testing of the suspensions prepared in Examples 2–6.

Splenectomized mice (BDF1) were injected once (subcutaneously) with 30 mg/kg of the various G-CSF-containing suspensions, and the various controls. The mice had their blood analyzed over several days. G-CSF powder (−glycerol) in 3% AIMS oil (30 mg/Kg); G-CSF powder in glycerol (30 mg/Kg); G-CSF powder dissolved in water (30 mg/Kg); and 1×PBS were run as controls. The data is summarized in Table 1 below.

TABLE 1

| | Neutrophil Count ($10^6$/mL) | | |
|---|---|---|---|
| Formulation | Day 3 | Day 5 | Day 7 |
| 1X PBS | 2.0 | 2.0 | 2.0 |
| G-CSF in pH 3.25 water (+5% sorbitol) | 2.0 | 2.0 | 2.0 |
| G-CSF in glycerol | 3.5 | 2.0 | 2.0 |
| G-CSF (−glycerol) in 3% AIMS/oil | 1.5 | 1.5 | 1.5 |

TABLE 1-continued

| Formulation | Neutrophil Count ($10^6$/mL) | | |
|---|---|---|---|
| | Day 3 | Day 5 | Day 7 |
| G-CSF/20% glycerol 3% AIMS/Oil | 24 | 33 | 19 |
| G-CSF/20% glycerol ascorbic acid/Span 80 3% AIMS/oil | 18.1 | 23.8 | 8.7 |
| G-CSF/20% glycerol 7% wax/oil | 27 | 40.2 | 10.3 |
| G-CSF/15% glycerol 7% wax/oil | 32.4 | 36 | 8.1 |
| G-CSF/25% glycerol 7% wax/oil | 24.6 | 38.2 | 13.9 |
| G-CSF/20% glycerol 10% wax/oil | 33.6 | 56.9 | 25.6 |

As evidenced by the data in Table 1, the polyol/thickened oil suspensions are capable of providing for the sustained release of G-CSF for periods of at least one week. Importantly, it should be noted that G-CSF could not be delivered in the oils without the addition of the polyol.

EXAMPLE 8

This example shows the preparation of an oils thickened with glycerin stearate.

Preparation 1: Glycerol tristearate (1.00 gram), glycerol monostearate (4.00 grams), and sesame oil (45.00 grams) were placed in a bottle and heated at 160° C. under nitrogen atmosphere for 2 hours. The mixture was then cooled to room-temperature while being vortexed. A white thickened oil was obtained.

Preparation 2: Glycerol monostearate (0.80 grams) and sesame oil (9.20 grams) were placed in a bottle and heated at 160° C. under nitrogen atmosphere for 2 hours. The mixture was then cooled to room temperature while being vortexed. A white thickened oil was obtained.

EXAMPLE 9

This example describes the preparation of thick oil using a mixture of sesame oil and the more viscous hydrogenated vegetable oil.

Sesame oil (6.00 mL) and hydrogenated vegetable oil (34.00 mL) were placed in a bottle and the mixture heated at 160° C. under nitrogen atmosphere for 2 hours. After the mixture cooled to room temperature, a thickened oil was obtained.

EXAMPLE 10

This example shows the preparation of G-CSF/glycerol in oil suspensions where the oil contains a mixture of sesame and hydrogenated vegetable oil and where the hydrogenated vegetable oil thickens the mixture.

Preparation 1: GCSF powder (10.0 mg) and glycerol (0.20 mL) were mixed, and then an oil mixture (hydrogenated oil/sesame oil=5/3, 0.80 mL) was added. The mixture was ground together with a mortar and pestle to give a viscous suspension formulation. This formulation was filled into a syringe and was syringable.

Preparation 2: GCSF powder (10.3 mg) and glycerol (0.20 mL) were mixed, and then an oil mixture (hydrogenated oil/sesame oil=3/17, 0.8 mL)) was added. The mixture was ground together with a mortar and pestle to give a viscous suspension formulation. This formulation was filled into a syringe and was syringable.

EXAMPLE 11

This example shows the preparation of a thickened oils using stearic acid, stearyl alcohol, and combinations thereof, as thickeners ±G-CSF/glycerol.

Preparation 1: Stearic acid (1.00 gram) and sesame oil (9.00 grams) were placed in a bottle and the mixture heated at 160° C. under nitrogen atmosphere for 2 hours. After cooling to room temperature with shaking the mixture became a viscous thickened oil.

Preparation 2: Stearyl alcohol (1.00 gram) and sesame oil (9.00 grams) were placed in a bottle and the mixture heated at 160° C. under a nitrogen atmosphere for 2 hours. After cooling to room temperature with shaking the mixture became a viscous thickened oil.

Preparation 3: Stearyl alcohol (0.50 grams), stearic acid (0.50 grams), and sesame oil (9.00 grams) are placed in a bottle and the mixture heated at 160° C. under nitrogen atmosphere for 2 hours. After cooling to room temperature with shaking the mixture became a viscous thickened oil.

Preparation 4: G-CSF powder (9.8 mg) and glycerol (0.20 mL) were mixed and then 0.80 mL of thickened oil (10% stearyl alcohol) was added. The mixture was ground for 10 minutes to give an oil formulation which was filled into a 1 mL syringe and was syringable.

Preparation 5: G-CSF powder (10.3 mg) and glycerol (0.20 mL) were mixed and then 0.80 mL of thickened oil (10% thickener, stearyl alcohol/stearic acid=3/1) was added. The mixture was ground for 10 minutes to give an oil formulation which was filled into a 1 mL syringe and was syringable.

EXAMPLE 12

This example shows the preparation of G-CSF containing aqueous glycerol in oil emulsion formulations where the G-CSF is mixed in the aqueous glycerol phase.

The water phase consisted of 12.7 mg/mL G-CSF, 50% glycerol, 1%(w/v) Pluronic F68, 10 mM acetate (pH 4.0) and 0.44 mM HCl. A mixture of 1% Pluronic L101 in corn oil formed the oil phase. A 50:50 and 70:30 mixture of the two phases were homogenized with a Virtis Handishear homogenizer for 45 seconds to form the respective emulsion formulations.

EXAMPLE 13

This example is prepared in a similar manner to Example 2 except the G-CSF dose is approximately 10 mg/Kg. After a single injection the neutrophils were elevated for at least one week.

What is claimed is:

1. A sustained-release pharmaceutical composition comprising granulocyte-colony stimulating factor (G-CSF) incorporated into a biocompatible polyol:oil suspension, wherein said suspension contains a thickener, and wherein said composition is prepared by a process which comprises:

(a) suspending G-CSF powder in a polyol to form a G-CSF:polyol mixture;

(b) suspending said G-CSF:polyol mixture in a mixture comprising a thickened oil to form a G-CSF:polyol:oil suspension; wherein the level of said polyol in said suspension is in the range from 15%–30% by weight.

2. The composition of claim 1 wherein said biocompatible polyol is selected from the group consisting of glycerol, erythritol, arabinose, xylose, ribose, inositol, fructose, galactose, maltose, and sucrose.

3. The composition of claim 1 wherein the thickener is selected from the group consisting of polyvalent metal salts of organic acids waxes and high viscosity oils.

4. The composition of claim 3 wherein the thickener is aluminum monostearate.

5. The composition of claim 3 wherein the thickener is white wax.

6. The composition of claim 1 wherein said oil is selected from the group consisting of sesame, castor, cottonseed, cannola, saffron, olive, peanut, sunflower seed, α-tocopherol, and ethyl oleate.

7. A process for preparing sustained-release pharmaceutical compositions of G-CSF:polyol:oil suspensions which comprises:

(a) suspending G-CSF powder in a polyol to form a G-CSF:polyol mixture;

(b) suspending said G-CSF:polyol mixture in a mixture comprising a thickened oil to form a G-CSF:polyol:oil suspension; wherein the level of said polyol in said suspension is in the range from 15%–30% by weight.

8. A method for the parenteral administration of G-CSF:polyol:oil suspension to a warm blooded animal, wherein said suspension is administered subcutaneously, or intramuscularly and the G-CSF is released from theto said animal suspension at a controlled rate for up to one week or more.

* * * * *

SEQUENCE LISTING

```
<160> NUMBER OF SEQ ID NOS: 1

<210> SEQ ID NO: 1
<211> LENGTH: 174
<212> TYPE: PRT
<213> ORGANISM: granulocyte colony-stimulating factor

<400> SEQUENCE: 1

Thr Pro Leu Gly Pro Ala Ser Ser Leu Pro Gln Ser Phe Leu Leu Lys
  1               5                  10                  15

Cys Leu Glu Gln Val Arg Lys Ile Gln Gly Asp Gly Ala Ala Leu Gln
             20                  25                  30

Glu Lys Leu Cys Ala Thr Tyr Lys Leu Cys His Pro Glu Glu Leu Val
         35                  40                  45

Leu Leu Gly His Ser Leu Gly Ile Pro Trp Ala Pro Leu Ser Ser Cys
     50                  55                  60

Pro Ser Gln Ala Leu Gln Leu Ala Gly Cys Leu Ser Gln Leu His Ser
 65                  70                  75                  80

Gly Leu Phe Leu Tyr Gln Gly Leu Leu Gln Ala Leu Glu Gly Ile Ser
                 85                  90                  95

Pro Glu Leu Gly Pro Thr Leu Asp Thr Leu Gln Leu Asp Val Ala Asp
            100                 105                 110

Phe Ala Thr Thr Ile Trp Gln Gln Met Glu Glu Leu Gly Met Ala Pro
        115                 120                 125

Ala Leu Gln Pro Thr Gln Gly Ala Met Pro Ala Phe Ala Ser Ala Phe
    130                 135                 140

Gln Arg Arg Ala Gly Gly Val Leu Val Ala Ser His Leu Gln Ser Phe
145                 150                 155                 160

Leu Glu Val Ser Tyr Arg Val Leu Arg His Leu Ala Gln Pro
                165                 170
```